United States Patent [19]

Walker

[11] Patent Number: 5,090,571
[45] Date of Patent: Feb. 25, 1992

[54] MEDICAL CONTAINER LINER

[75] Inventor: Michael R. Walker, Warsaw, Ind.

[73] Assignee: Zimmer, Inc., Warsaw, Ind.

[21] Appl. No.: 670,138

[22] Filed: Mar. 15, 1991

[51] Int. Cl.$^5$ .................. B65D 85/30; B65D 81/02
[52] U.S. Cl. ............................ 206/523; 206/438;
 220/902; 220/448; 229/126; 229/128; 229/127
[58] Field of Search ............... 206/523, 438; 220/902,
 220/448; 229/126, 127, 128

[56] References Cited

U.S. PATENT DOCUMENTS

| 3,309,893 | 3/1987  | Heffler et al. | 206/523 X |
| 3,516,596 | 6/1970  | Madden et al. | 206/523 X |
| 4,697,703 | 10/1987 | Will          | 206/438   |
| 4,750,619 | 6/1988  | Cohen et al.  | 206/438   |
| 4,953,705 | 9/1990  | Evamy         | 206/523 X |
| 5,002,184 | 3/1991  | Lloyd         | 206/523   |

FOREIGN PATENT DOCUMENTS 930959 2/1948 France .................. 229/126

OTHER PUBLICATIONS

Zimmer, Inc.—Drawing—Die Cut Foam Pad Liner—1984.
Zimmer, Inc.—Drawing—Foam Envelope—1982.

Primary Examiner—William I. Price
Attorney, Agent, or Firm—Gary R. Reeves; Margaret L. Geringer

[57] ABSTRACT

A separate protective liner for sterile medical device containers comprises a bottom, walls and a lid to encapsulate the medical device. The lid and walls cooperate to form an interference fit thereby maintaining the lid in a closed position without the need for any additional lid closure mechanism.

15 Claims, 4 Drawing Sheets

MEDICAL CONTAINER LINER

BACKGROUND OF THE INVENTION

The present invention relates to packaging materials for medical devices. More specifically, it relates to separate protective liners for medical device containers which are commonly employed to protect the device from shock and abrasion during handling. These liners, which may be particularly suitable for sterile packaging of devices, also protect the container from damage from the medical device that would result in a breach of the sterile environment inside the container.

It is important for medical containers, as well as protective liners, to be easy to open and handle for gloved individuals, such as surgical staff. After having been opened, liners and other packaging materials may typically be discarded. Being disposable, as well as being manufactured in large quantities, these protective liners must also be inexpensive and easily assembled.

The medical field has attempted to provide these functions and features in various ways. One such example is to place a medical device into a foam envelope. The device and envelope are next placed into a container forming a snug fit between the envelope and container to immobilize the device. Finally, a cover is placed on the container and the container and cove are moved into a machine that applies heat and pressure to seal the cover in place. To facilitate sealing, the device and foam envelope must not protrude above the rim of the container. In use, the cover is peeled from the container within an operating room and the product and envelope are removed. This can be difficult due to the snug fit of the envelope in the container; difficulty in removal of the device can lead to dropping or otherwise contaminating it, thereby rendering it useless. After removal from the container, the envelope is carefully removed from the device, requiring more handling.

To simplify device removal, an alternate liner is sometimes used. This alternative comprises a box-shaped foam liner, either a one-piece unit or a more economical die cut foldable unit, that conforms to the shape of the container. This type of conforming liner does not cling to the device like an envelope, and therefore eases removal of the device therefrom. However, the conforming liner preferably must be provided with a lid and a means to securely close the lid so as to avoid interference with the sealing process. In U.S. Pat. No. 4,750,619, Cohen et al. shows a die cut liner of this sort. Cohen's liner comprises a bottom with integral side and end walls and a lid extending from one of the end walls such that the liner is foldable into a box shape with the lid coming to rest atop the walls. Cohen further provides a tray to enclose the liner, the tray including hinged leaves that maintain the liner in a closed position when the tray and liner are placed in the container. It can be seen that this more complicated arrangement requires an additional component, namely the tray, and subsequently additional cost to confine the liner. Additionally, the tray and liner must be removed from the container to access the device which requires the troublesome handling of several package components.

SUMMARY OF THE INVENTION

The present invention provides a separate protective liner for medical device containers comprising a bottom, walls, and a lid to encapsulate the medical device. The lid and walls cooperate to form an interference fit, thereby maintaining the lid in a closed position without the need for any other additional lid closure mechanism. The medical device containers of the present invention may be utilized to package various medical devices such as knee or hip implant components, surgical instruments, or any other suitable device.

The present invention improves upon the prior art through its any objects and advantages which include but are not limited to protection of a medical device within its container and preservation of the container sterile environment during handling of the container; ease of assembly and simplicity of design to yield a low package cost; ability to maintain a low liner profile during the package sealing process without the need for adhesives on the liner, additional package components or other means; and ease of opening by the end user to fully expose the medical device while not requiring removal of the liner from the container and thereby reducing the risk of dropping or otherwise contaminating the device.

BRIEF DESCRIPTION OF THE DRAWINGS

These objects and advantages of the present invention will be apparent from the following detailed description and the drawings wherein.

DETAILED DESCRIPTION OF THE INVENTION

Figure 1:
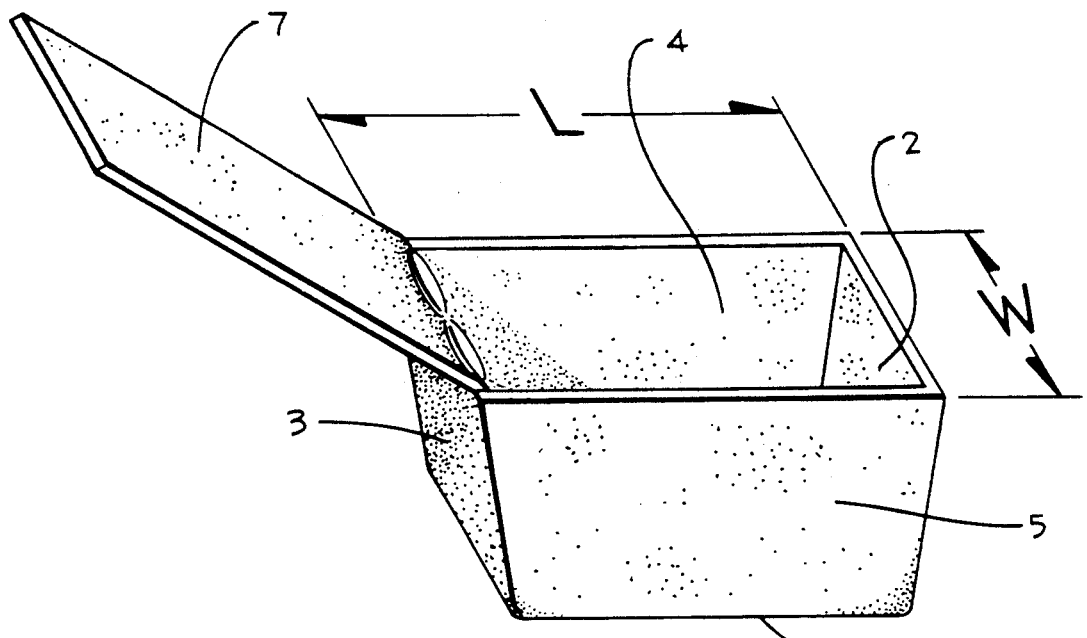
FIG. 1 is a perspective view of an embodiment of the present invention with the lid in the open position.
Figure 2:
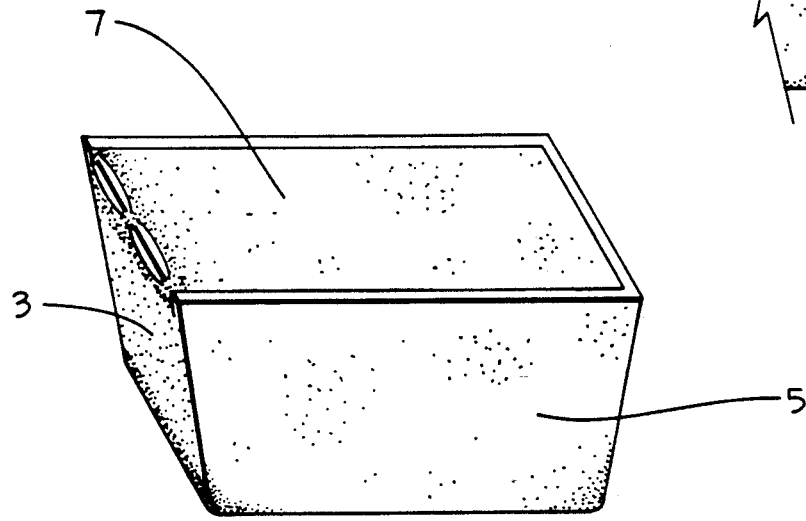
FIG. 2 is a perspective view of the embodiment of FIG. 1, but with the lid shown in the closed position.

Referring to FIG. 1, a typical liner 50 for sterile medical device containers in accordance with the present invention comprises a bottom 1 with upwardly extending spaced apart end walls 2 and 3 and side walls 4 and 5 defining a cavity with an opening at the top to receive the medical device. The width "W" of end walls 2 and 3 defines the latitudinal direction, and the length "L" of the side walls 4 and 5 defines the longitudinal direction. End wall 3 extends beyond the cavity opening to form a lid 7 which can be folded downwardly to close the opening. Lid 7 is slightly larger than the cavity opening in the latitudinal direction and essentially the same size as the opening in the longitudinal direction. This particular sizing arrangement produces an interference fit between lid 7 and side walls 4 and 5 thereby maintaining lid 7 in the closed position as shown in FIG. 2 without the need of additional packaging components. The liner 50 may preferably be made of a cushioning or resilient material, such as a flexible plastic foam, to aid the lid in fitting snugly between the walls. The lid 7, is substantially flush with the upper edge of the walls of the liner when closed, thus fitting between the top edges of side walls 4 and 5 rather than resting upon them.

Figure 3:
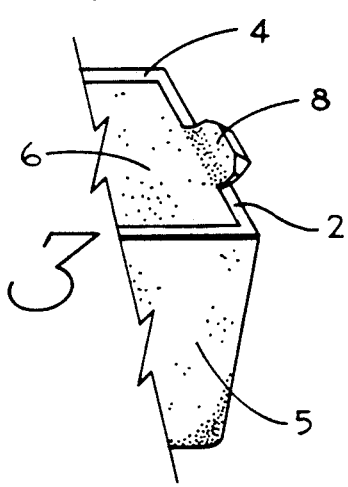
FIG. 3 is a fragmentary perspective view showing a modified form of the closed lid of FIG. 2.

Turning to FIG. 3, an alternate lid 6 provides a tab 8 formed at its free end and extending outwardly longitudinally such that as lid 6 is pressed closed end wall 2 contacts tab 8 on its undersurface, thereby forcing it upwardly and providing a grasping means for easily opening the liner.

Figure 4:
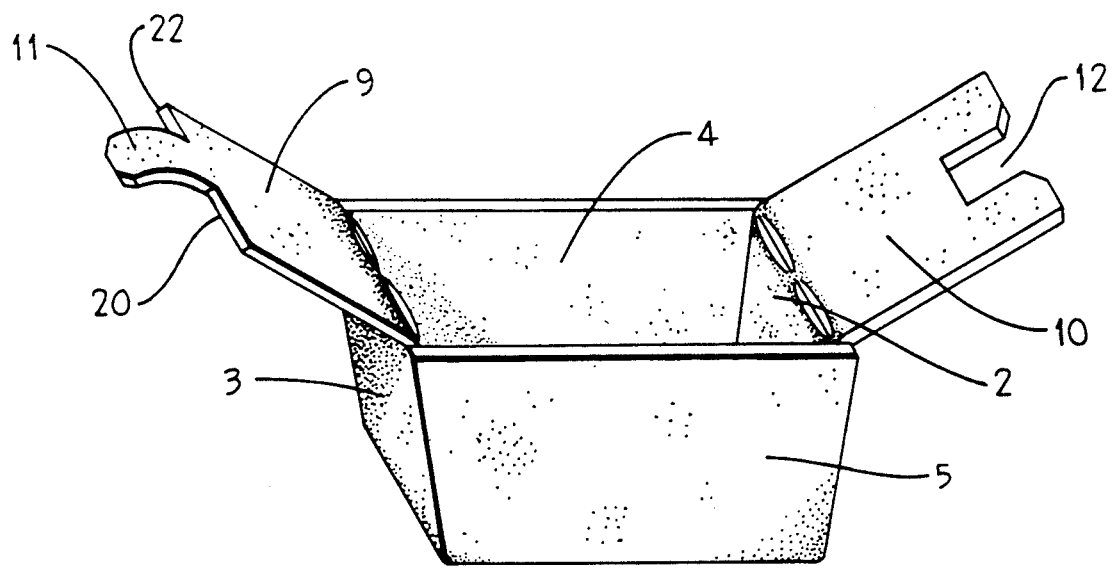
FIG. 4 is a perspective view showing an alternate embodiment with the lid comprising two half lids, one containing a tab and the other containing a slot.
Figure 6:
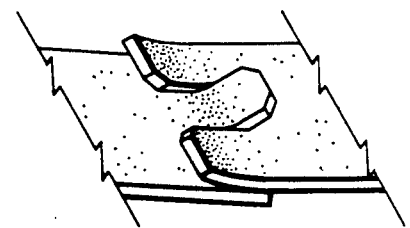
FIG. 6 is a fragmentary perspective view showing lid detail
Figure 5:
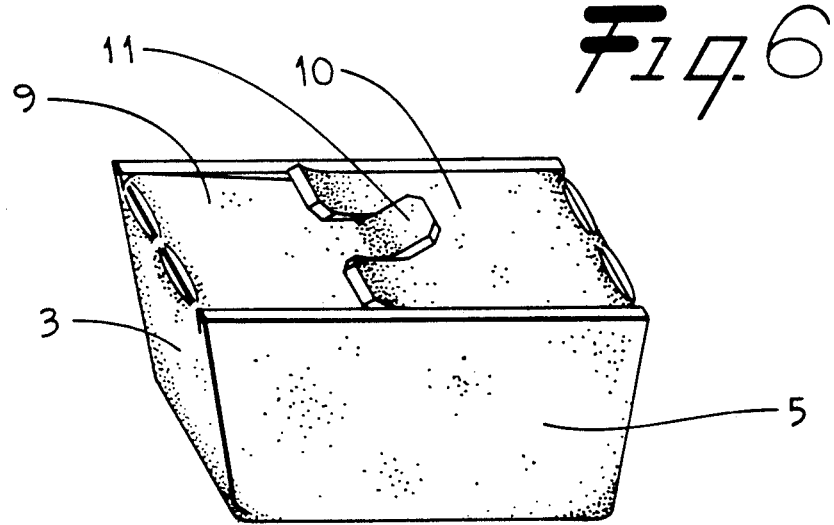
FIG. 5 is a perspective view of the embodiment of FIG. 4; but with the lid shown in the closed position.

FIG. 4 depicts a further modified liner lid wherein the lid comprises two lid halves 9 and 10. Lid half 9 is formed as an extension of end wall 3 and further forms a tab 11 extending outwardly longitudinally from its free end, whereas lid half 10 is formed as an extension of end wall 2 and includes an open slot 12 extending inwardly longitudinally from its free end. Lid halves 9 and 10 are slightly larger than the cavity opening latitudinally and tab 11 and slot 12 have substantially the same latitudinal dimension such that as the lid is closed tab 11 engages slot 12 to maintain latitudinal tension in lid halves 9 and 10 thereby allowing an interference fit along the side walls 4 and 5 to maintain the lid in a closed position as in FIG. 5. Lid halves 9 and 10 may overlap when closed as in FIG. 6. It can be seen that if the lid is closed with tab 11 outside the cavity, tab 11 forms an easily grasped opening means. However, it is also understood that if the lid is closed with tab 11 inside the cavity (not shown), end portion 20 or 22 of lid half 9 will form an easily grasped opening means. The lid arrangement of FIGS. 4–6 is the preferred lid arrangement as it is convenient and is easily opened. The liners of FIG. 1–6 may be formed by machining and heat forming or by any other suitable means.

Figure 7:
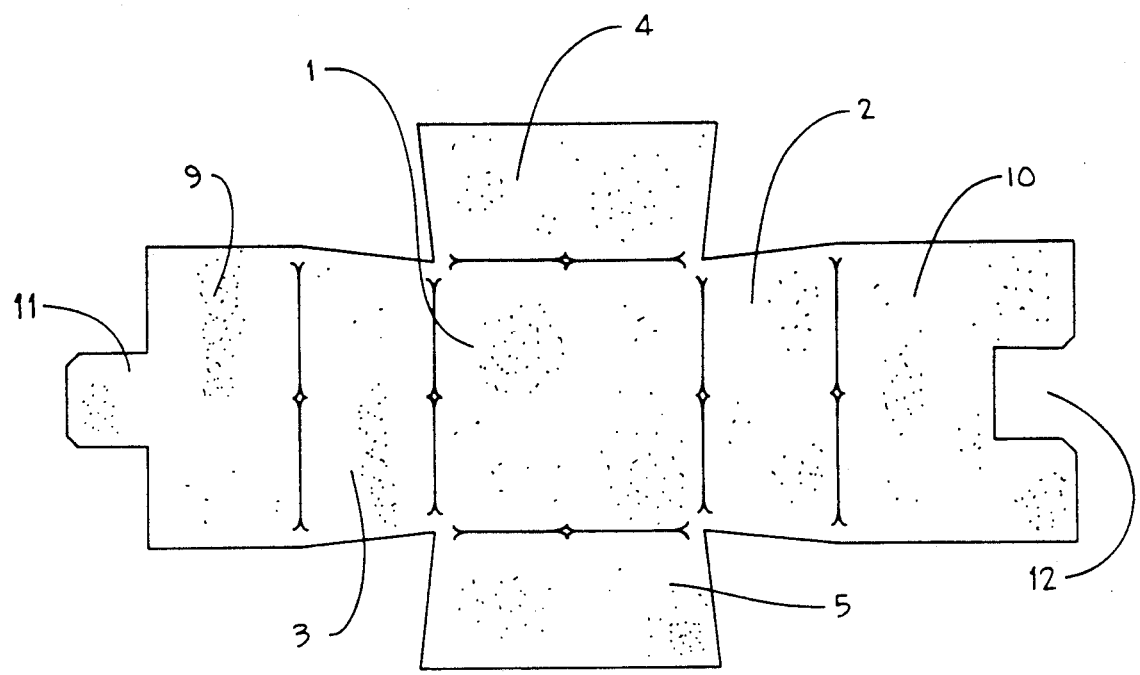
FIG. 7 is a plan view of the preferred embodiment comprising a die cut foldable liner.

FIG. 7 represents a plan view of a die cut liner in the unfolded position. Die cut liners are preferred for their economy of manufacture. The die cut liner may be scored at the folding lines of the liner to aid in folding the liner to its desired shape.

Figure 8:
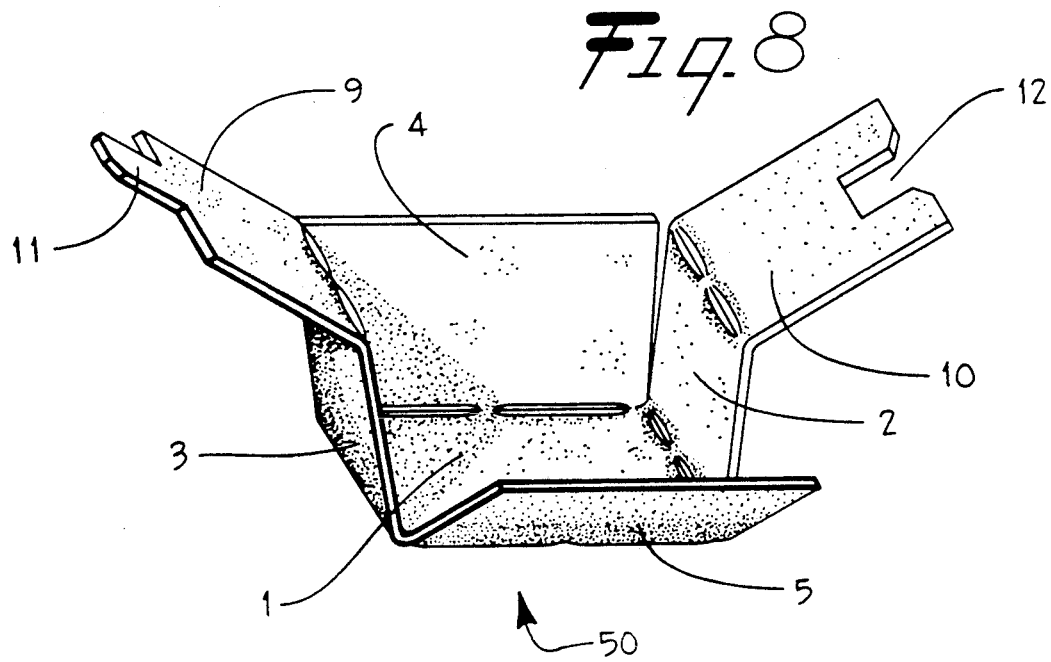
FIG. 8 is a perspective view of the preferred embodiment showing a die cut foldable liner in a partially folded position including a lid comprising two half lids, one forming a tab and the other containing a slot.

FIG. 8 shows a partially folded liner embodiment comprising all of the preferred features heretofore described including a die cut liner with a lid comprising two lid halves 9 and 10 with tab 11 and slot 12. It should be noted that the walls of the liner of FIG. 8 are held in abutment with one another when it is placed into the container which it lines, such as in FIG. 9. Additionally it is desirable for the liner 50 to be formed of a plastic foam material, such as a cross-linked polyethylene foam, so that it will provide cushioning for the medical device and protection of its surface finish, although any suitable cushioning or other material may be utilized, as desired.

Figure 9:
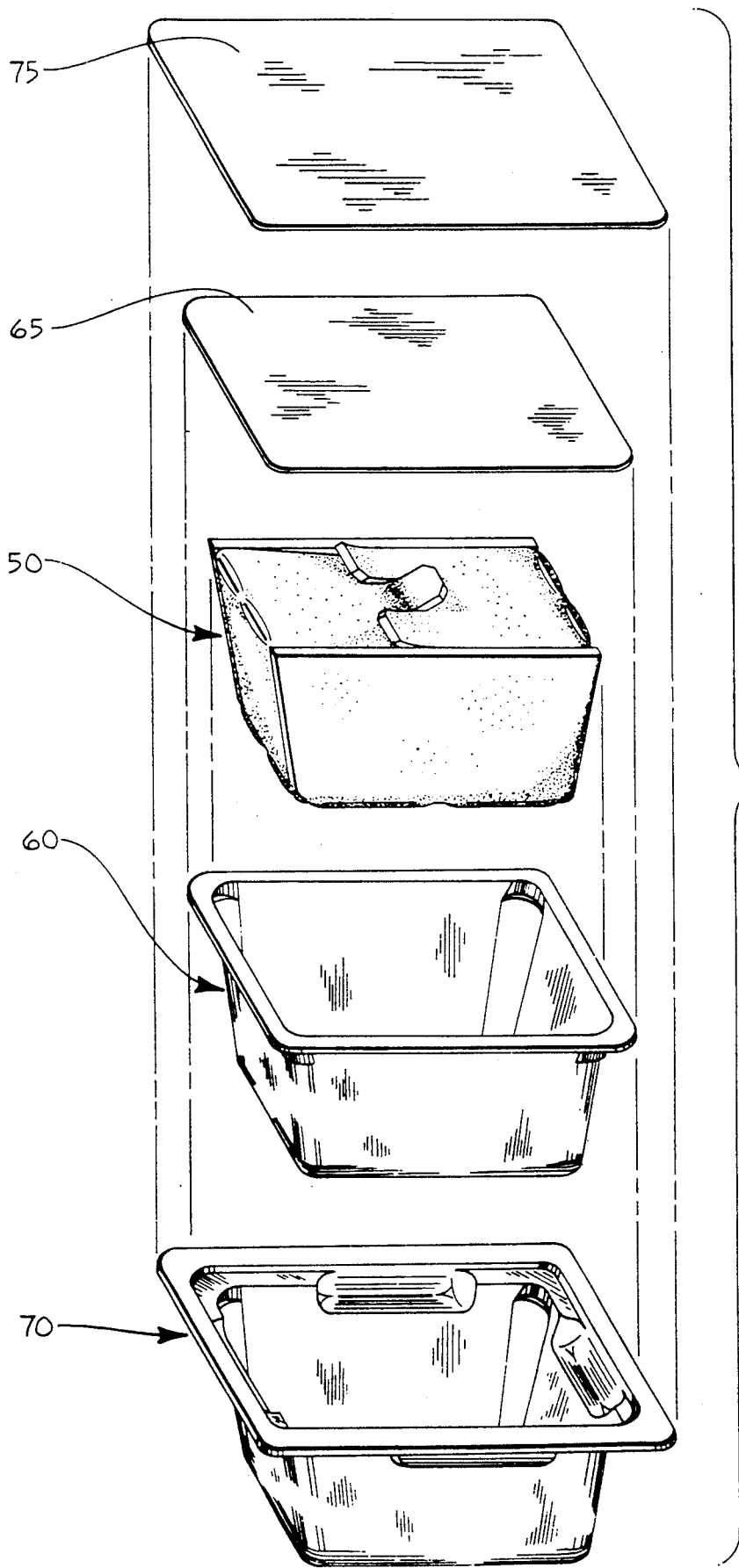
FIG. 9 is an exploded perspective view of the liner of FIG. 8 shown with other packaging materials, as may be used with the preferred embodiment.

FIG. 9 illustrates the die cut liner of FIG. 8 with other suitable packaging materials that may be appropriately used with applicant's inventive liner. The liner 50 fits snugly in inner container 60. The container 60 helps maintain the walls of the die cut liner in position to form the liner cavity. The snug fit of liner 50 within container 60 aids in the press-fitting of the lid within the cavity of the liner. The cover 65 may then be sealed to inner container 60, as is known in the art. Inner container 60 may further be placed in an outer container 70 which is sealed with cover 75 for the additional protection of a double-sealed container. The whole assembly may then be sterilized, if desired, in accordance with typical industry practice. Alternately, the liner 50 may be snugly fitted into any suitable medical device container, other than the type shown in FIG. 9, as desired.

This detailed description is intended to be an example for illustrative purposes only. It will be understood by those skilled in the art that numerous modifications may be made to the preferred embodiment without departing from the spirit and scope of the invention defined by the appended claims.

I claim:

1. A liner to fit within a container and encapsulate a medical device, wherein the liner comprises a bottom with upwardly extending spaced apart end walls and side walls defining a cavity with an opening at the top to receive the medical device, the end wall width defining the latitudinal direction and the side wall length defining the longitudinal direction, at least one of said end walls extending beyond the opening to form a lid which can be folded downwardly to close the opening and complete the encapsulation of the medical device, wherein the lid extension is larger than the opening in the latitudinal direction such that the lid can be pressed into the opening to form an interference fit along the side walls thereby maintaining the lid in a closed position.

2. The liner of claim 1 wherein the lid includes a tab extending outwardly longitudinally from its free end, such that when the lid is closed, the tab overhangs the end wall adjacent its free end to provide an easily grasped means to open the lid.

3. The liner of claim 1 wherein both end walls extend beyond the opening, each forming one-half of a lid, one of the halves including a tab extending outwardly longitudinally from its free end and the other half including a slot extending inwardly longitudinally from its free end, wherein the slot and tab have essentially the same latitudinal dimension, such that as the lid is pressed closed the tab engages the slot to maintain lid tension latitudinally and the lid forms an interference fit along the side walls to maintain the lid in a closed position.

4. The liner of claim 3 being formed from a plastic foam material thereby providing cushioning and abrasion protection for the medical device.

5. A liner to fit within a container and encapsulate a medical device wherein the liner is formed by die cutting a flat sheet of material to define a bottom with integral side walls, end walls and a lid extending from at least one of said end walls; the die cut sheet being foldable to form an upright liner with side walls and end walls extending upwardly from said bottom defining a cavity with an opening at the top; the upright position of the liner being maintained by the adjacent walls of the container; the end wall width of the upright liner defining the latitudinal direction and the side wall length defining the longitudinal direction; the liner lid being foldable to close the opening and complete encapsulation of the medical device; the lid having a larger latitudinal dimension than the opening such that the lid can be pressed into the opening to form an interference fit along the side walls thereby maintaining the lid in a closed position.

6. The liner of claim 5 wherein both end walls extend beyond the opening, each forming one-half of a lid, one of the halves including a tab extending outwardly longitudinally from its free end and the other half including a slot extending inwardly longitudinally from its free end, wherein the slot and tab have essentially the same latitudinal dimension, such that as the lid is pressed closed, the tab engages the slot to maintain lid tension latitudinally and the lid forms an interference fit along the side walls to maintain the lid in a closed position.

7. The liner of claim 5 being formed, from a plastic foam material thereby providing cushioning and abrasion protection for the medical device.

8. A protective liner to fit within a medical device container to encapsulate the medical device wherein the liner is of a single-piece and includes a bottom with a wall extending upwardly therefrom to a top end defining a cavity an opening at the top end to receive the medical device, a of the wall means extends beyond the opening to form a lid which be folded downwardly to close the opening, wherein the lid is larger than the opening and wherein the liner is made of a resilient material, such that the lid can be pressed into the opening to form an interference fit with the wall means, thereby maintaining the lid in a closed position.

9. The liner of claim 8 wherein the lid includes a tab extending outwardly from a free end of the lid, such that when the lid is closed, the tab extends above the wall means to provide a grasping means for assisting in opening the lid.

10. The liner of claim 8 wherein the liner includes two oppositely located sides and the wall means extends beyond the opening from each of these oppositely located sides, each forming one-half of the lid.

11. The liner of claim 10 wherein one of the lid halves includes an outwardly extending tab and the other of the lid halves includes a corresponding inwardly extending recess, such that when the lid is closed, the tab fits securely within the recess to maintain the lid in a closed position.

12. The liner of claim 11 wherein the two lid halves overlap in the closed position.

13. The liner of claim 8 wherein the liner is formed from a single die cut sheet of resilient material.

14. The liner of claim 8 wherein the liner is made by heat forming to a die.

15. The liner of claim 8 wherein the liner fits snugly within an outer walled receptacle.

* * * * *